US007833704B2

(12) United States Patent
Wildenberg et al.

(10) Patent No.: US 7,833,704 B2
(45) Date of Patent: Nov. 16, 2010

(54) METHODS FOR DETECTING ANEUPLOIDY USING MICROPARTICLE MULTIPLEX DETECTION

(75) Inventors: Andrew Patrick Wildenberg, Mount Vernon, IA (US); Karl Poetter, Northcote (AU)

(73) Assignee: Genera Biosystems Limited (AU)

( * ) Notice: Subject to any disclaimer, the term of this patent is extended or adjusted under 35 U.S.C. 154(b) by 0 days.

(21) Appl. No.: 10/563,550

(22) PCT Filed: Jul. 2, 2004

(86) PCT No.: PCT/AU2004/000894

§ 371 (c)(1),
(2), (4) Date: Jul. 5, 2006

(87) PCT Pub. No.: WO2005/003380

PCT Pub. Date: Jan. 13, 2005

(65) Prior Publication Data

US 2007/0015159 A1    Jan. 18, 2007

(30) Foreign Application Priority Data

Jul. 4, 2003    (AU) .............................. 2003903417

(51) Int. Cl.
*C12Q 1/68* (2006.01)
(52) U.S. Cl. .......................... 435/6; 436/501; 436/164; 436/172
(58) Field of Classification Search ................... None
See application file for complete search history.

(56) References Cited

U.S. PATENT DOCUMENTS

| 5,756,696 | A | 5/1998 | Gray et al. | |
|---|---|---|---|---|
| 6,562,565 | B1* | 5/2003 | Pinkel et al. .................... | 435/6 |
| 6,787,307 | B1* | 9/2004 | Bitner et al. ..................... | 435/6 |
| 2003/0124584 | A1* | 7/2003 | Mohammed ..................... | 435/6 |
| 2007/0015159 | A1* | 1/2007 | Wildenberg et al. .............. | 435/6 |
| 2008/0102455 | A1* | 5/2008 | Poetter ........................... | 435/6 |

FOREIGN PATENT DOCUMENTS

| WO | WO 95/08646 | 3/1995 |
|---|---|---|
| WO | WO 97/14028 A | 4/1997 |
| WO | WO 01/27328 A1 | 4/2001 |
| WO | WO 02/40698 A | 5/2002 |
| WO | WO 02/068685 | 9/2002 |

OTHER PUBLICATIONS

Ibanez E, et al. Assessment of the proportion of transgene-bearing sperm by fluorescence in situ hybridization: a novel approach for the detection of germline mosaicism in transgenic male founders. Mol Reprod Dev. Feb. 2001;58(2):166-72.*
Gvakharia M, et. al. Single in vitro fertilization (IVF) cycle with blastomere biopsy for preimplantation genetic diagnosis (PGD) of Huntington's disease, assisted hatching and cryopreservation results in healthy baby and subsequent ongoing pregnancy. Fertility and Sterility. Sep. 2002; 78(Supplement 1):S229.*
Bianchi et al., *Prenat. Diag.* 22(7):609-615 (2002).
Bonner and Laskey, *Eur. J. Biochem* 46:83-88 (1974).
Cook, E.B. et al., Simultaneous measurement of six cytokines in a single sample of human tears using microparticle-based flow cytometry: allergics vs. non-allergics. *Journal of Immunological Methods,* 254:109-118 (2001).
Gray, J.W. et al., *Clinical Chemistry,* 21(9): 1258-1262 (1975).
He, H. et al., *International Journal of Radiation Biology,* 77(7):787-795 (2001).
Kraus, M. et al., *E Experimental Technique of Physics/Experimentelle Technik Der Physik,* 41(1):139-153 (1995).
Lomax, B. et al., Comparative genomic hybridization in combination with flow cytometry improves results of cytogenetic analysis of spontaneous abortions. *American Journal of Human Genetics* 66:1516-1521 (2000).
Marmur and Doty, J. Mol. Biol. 5:109-118 (1962).
Schmidt, W. et al., *Mol. Hum. Reprod.* 6(9):855-860 (2000).
Spiro, A. et al., A bead-based method for multiplexed identification and quantification of DNA sequences using flow cytometry, *Applied and Environmental Microbiology* 66(10):4258-4265 (2000).
Stepanov, S.I. et al., *Cytometry,* 23(4): 279-283 (1996).
Trask, B. et al., *Cytometry* 11:184-195. (1990).
Voojis, M. et al., AM. J. Hum. Genet. 52: 586-597 (1993).
Wilton, L., Preimplantation genetic diagnosis for aneuploidy screening in early human embryos: a review, *Prenatal Diagnosis* 22:512-518 (2002).
Spiro, et al, A Bead-Based Method for Multiplexed Identification and Quantitation of DNA Sequences Using Flow Cytometry, Applied and Environmental Biology, Oct. 2000, p. 4258-4265, vol. 66, No. 10.

* cited by examiner

*Primary Examiner*—Carla Myers
(74) *Attorney, Agent, or Firm*—The McCallum Law Firm, P.C.; Jennifer M. McCallum, Esq.

(57) ABSTRACT

The present invention provides a method for the detection and sorting of microparticles in a mixture of microparticles. The method of the present invention allows for the detection and sorting of many distinct microparticle classes. Detection and sorting is on the basis of microparticle size, the fluorescence spectrum of any attached reporter molecule, the fluorescence intensity of the reporter molecule, and the number of particles in each classification bin. These microparticle classes have particular applications in many genetic or biochemical multiplexing studies and especially as binding agents for the detection of aneuploidy in an organism or embryo of the organism. In humans, the detection and sorting of at least 24 classes of microparticles would be sufficient for a single tube method for the simultaneous detection of aneuploidy in all chromosomes, wherein each distinct microparticle class comprises a polynucleotide sequence complementary to, and specific for, a polynucleotide sequence that is unique to a particular human chromosome. Furthermore, using currently available technology, the present method has application for the simultaneous detection of aneuploidy in all chromosomes for an organism that has 216 or fewer pairs of chromosomes. Kits for the simultaneous detection of aneuploidy in one or more human chromosomes are also provided.

11 Claims, 7 Drawing Sheets

BC     Genotype

50   Heterozygote
25   Homozygous G

FIGURE 4

BC | Genotype
---|---
50 | Homozygous A
25 | PCR Fail

FIGURE 5

BC     Genotype

50   Homozygous A
25   Heterozygote

FIGURE 6

| BC | Genotype |
| --- | --- |
| 50 | Homozygous A |
| 25 | Homozygous A |

FIGURE 7

| BC | Genotype |
|---|---|
| 50 | Homozygous G |
| 25 | Homozygous A |

METHODS FOR DETECTING ANEUPLOIDY USING MICROPARTICLE MULTIPLEX DETECTION

The present application is a U.S. national phase filing under 35 U.S.C. 371 of PCT Application No. PCT/AU2004/000894, filed Jul. 2, 2004, which claims the benefit of Australian Application No. 2003903417, filed Jul. 4, 2003, each of which are hereby incorporated by reference in their entirety.

BACKGROUND OF THE INVENTION

1. Field of the Invention

The present invention provides a method for the detection and sorting of microparticles in a mixture of microparticles. The method of the present invention allows for the detection and sorting of many distinct microparticle classes. Detection and sorting is on the basis of microparticle size, the fluorescence spectrum of any attached reporter molecule, the fluorescence intensity of the reporter molecule, and the number of particles in each classification bin. These microparticle classes have particular applications in many genetic or biochemical multiplexing studies and especially as binding agents for the detection of aneuploidy in an organism or embryo of the organism. In humans, the detection and sorting of at least 24 classes of microparticles would be sufficient for a single tube method for the simultaneous detection of aneuploidy in all chromosomes, wherein each distinct microparticle class comprises a polynucleotide sequence complementary to, and specific for, a polynucleotide sequence that is unique to a particular human chromosome. Furthermore, using currently available technology, the present method has application for the simultaneous detection of aneuploidy in all chromosomes for an organism that has 216 or fewer pairs of chromosomes. Kits for the simultaneous detection of aneuploidy in one or more human chromosomes are also provided.

2. Description of the Prior Art

Bibliographic details of the publications referred to in this specification are also collected at the end of the description.

Reference to any prior art in this specification is not, and should not be taken as, an acknowledgment or any form of suggestion that this prior art forms part of the common general knowledge in any country.

Under normal circumstances in a diploid organism, one chromosome from each parent is transmitted to the offspring embryo. However, non-disjunction events, on the maternal, paternal or both sides can lead to embryos with aberrant chromosome number, a condition known as aneuploidy.

Euploidy is the condition of having a correct number of structurally normal chromosomes. For example, euploid human females have 46 chromosomes (44 autosomes and two X chromosomes), whereas euploid bulls have 60 chromosomes (58 autosomes plus an X and a Y chromosome).

Aneuploidy is the condition of having less than or more than the natural diploid number of chromosomes, and is the most frequently observed type of cytogenetic abnormality. In other words, it is any deviation from euploidy, although many authors restrict use of this term to conditions in which only a small number of chromosomes are missing or added.

Generally, aneuploidy is recognized as a small deviation from euploidy for the simple reason that major deviations are rarely compatible with survival, and such individuals usually die prenatally.

The two most commonly observed forms of aneuploidy are monosomy and trisomy.

Monosomy is lack of one of a pair of chromosomes. An individual having only one chromosome 6 is said to have monosomy 6. A common monosomy seen in many species is X chromosome monosomy, also known as Turner's syndrome in humans. Monosomy is most commonly lethal during prenatal development.

Trisomy is having three chromosomes of a particular type. A common autosomal trisomy in humans is Down syndrome, or trisomy 21, in which a person has three instead of the normal two chromosome 21's. Trisomy is a specific instance of polysomy, a more general term that indicates having more than two of any given chromosome (in diploid organisms).

Another type of aneuploidy is triploidy. A triploid individual has three of every chromosome, that is, three haploid sets of chromosomes. A triploid human would have 69 chromosomes (3 haploid sets of 23), and a triploid dog would have 117 chromosomes. Production of triploids seems to be relatively common and can occur by, for example, fertilization by two sperm. However, birth of a live triploid is extraordinarily rare and such individuals are quite abnormal. The rare triploid that survives for more than a few hours after birth is almost certainly a mosaic, having a large proportion of diploid cells.

A chromosome deletion occurs when the chromosome breaks and a piece is lost. This of course involves loss of genetic information and results in what could be considered "partial monosomy" for that chromosome.

A related abnormality is a chromosome inversion. In this case, a break or breaks occur and that fragment of chromosome is inverted and rejoined rather than being lost. Inversions are thus rearrangements that do not involve loss of genetic material and, unless the breakpoints disrupt an important gene, individuals carrying inversions have a normal phenotype.

In a monosomic sample, with 2 n−1 chromosomes, one entire chromosome and all its loci are lost. Similarly, in a 2 n+1 trisomic sample, one extra chromosome is present in each cell, meaning one specific chromosome is represented three times due to a non-dysjunction event, usually in the female gametogenesis. A similar, but more pronounced, situation occurs in the case of a triploid sample in which each chromosome is represented three times instead of twice in each cell.

Pregnancies can be established in infertile women using the technique of in-vitro fertilization (IVF). In spite of the high rate of fertilization in-vitro, the rate of pregnancy following these procedures is relatively low, ranging from 15% to 25%. Cytogenetic studies of human oocytes fixed after failing to fertilize in-vitro display a relatively high incidence of chromosomal abnormalities (aneuploidy). Also, studies of many spontaneous abortions and pre-term embryos show that chromosomal abnormalities may be the main cause of fetal loss. The frequency of chromosomal abnormality in embryos generated using IVF is much higher than total abnormalities reported for sperm and oocytes.

In the IVF procedure, aneuploidy is the most frequently observed abnormality in the embryos generated. Many reports strongly indicate that chromosomal aneuploidy is the prime cause of fertilization failure in oocytes and implantation failure of embryos. Aneuploidy mainly arises during meiotic non-dysjunction; but many environmental factors may also disrupt spindle function and eventually lead to the formation of aneuploid embryos.

Using methods currently known in the art to assess the embryo's gross chromosome makeup, one would perform cytogenetic analyses, such as karyotyping. However, this method is not a practical solution for single cells, and therefore cannot be performed as a pre-implantation screen.

Therefore, there is a need to develop rapid, inexpensive, automatable methods for detecting aneuploidy in an embryo that can be applied in the pre-implantation setting for in-vitro fertilization. The present invention provides a method, which has application, inter alia, as a rapid, single-tube method for the simultaneous detection of aneuploidy in one, multiple or all chromosomes of a subject.

In particular, this method may increase the success rates of IVF, as embryos with aberrant chromosome numbers (aneuploid) could be screened out by a pre-implantation scan of the embryogenic genetic component.

SUMMARY OF THE INVENTION

The present invention provides a method for the detection and sorting of microparticles in a mixture of microparticles. The method of the present invention allows for the detection and sorting of many distinct microparticle classes. Detection and sorting is on the basis of microparticle size, the fluorescence spectrum of any attached reporter molecule, the fluorescence intensity of the reporter molecule. A fourth delimiter is the number of particles in a particular class. It is possible to multiplex experiments on microspheres by using replicate numbers to differentiate results of separate experiments. These microparticle classes have particular application as binding agents for the detection of aneuploidy in an organism or embryo of the organism. In humans, the detection and sorting of at least 24 classes of microparticles would be sufficient for a single tube method for the simultaneous detection of aneuploidy in all chromosomes, wherein each distinct microparticle class comprises polynucleotide sequence(s) complementary to, and specific for, a polynucleotide sequence that is unique to a particular human chromosome. Furthermore, using currently available technology, the present method has application for the simultaneous detection of aneuploidy in all chromosomes for an organism that has 216 or fewer pairs of chromosomes. Kits for the simultaneous detection of aneuploidy in one or more human chromosomes are also provided.

The present is predicated, in part, by a method for the multiplex detection and sorting of several distinct classes of microparticle from a mixture of microparticles on the basis of microparticle size, any label present on the microparticle, the intensity of the label and the number of particles present.

The present inventors have identified that it is possible to differentiate the intensity of a given fluorescent label on a microparticle of a particular size. Additionally, the present inventors have produced microparticles with six different fluorescence intensities for a given label. Further, discrimination of events can be performed based on particle number.

Accordingly, by concatenation of the microparticle size data and fluorescence intensity data, the present invention provides a method for the differentiation of 36 different microparticle classes for a single-labeled microparticle. However, the present invention also encompasses multiple labelled microparticles, such as dual-labelled microparticles which can be then separated into at least 216 classes. Further, the present invention allows for unlimited classes based on discrimination classifications based on particle numbers.

Accordingly, the present invention contemplates a method for the detection and sorting of labelled or unlabelled microparticles from a mixture of microparticles on the basis of one or more of the following characteristics:

(i) microparticle size
(ii) microparticle label
(iii) microparticle label intensity
(iv) microparticle number In a preferred embodiment, microparticles are detected and/or sorted according to the method of the present invention using flow cytometry.

A particularly preferred application of the present invention is the multiplex detection of aneuploidy in one or more chromosomes of an organism or embryo of an organism simultaneously.

If a given amount of DNA representing a particular chromosome number from a known control diploid DNA is competed against a like amount of DNA from a given biological sample for a limiting number of binding targets, the DNA's should bind to the targets in their relative frequencies.

In order to differentiate the standard from the sample for the purposes of the present invention, it is preferred that the labels for the sample and the standard have distinct emission spectra. In addition, when part of a multiplex reaction, the fluorescence spectra of the label of the sample and standard must be distinct from the fluorescence spectrum or spectra of the label(s) attached to the binding agent.

Accordingly, the present invention provides a method for detecting aneuploidy in one or more chromosomes of a subject simultaneously, said method comprising:

(i) producing reporter molecule-labelled polynucleotide samples that are representative of the abundance of each chromosome in said subject;
(ii) producing equivalent, non-aneuploid polynucleotide standards for each chromosome, labelled with a different reporter molecule;
(iii) mixing said samples and said standards with a limiting amount of binding agent for each chromosome, wherein said binding agents comprise a polynucleotide that is complementary to the sample and standard for each chromosome wherein the binding agent polynucleotide is immobilized onto a microparticle, and the microparticles associated with the polynucleotide sequence for each chromosome are distinct on the basis of size and/or fluorescent label and/or fluorescent label intensity;

wherein the fluorescent label on the microparticle, if present, has a distinct emission spectrum from both the label of the sample and standard; and wherein aneuploidy is detected as non-equal binding of the sample and standard to the binding agent.

Simultaneous detection of aneuploidy in all chromosomes of the organism is possible using the multiplex detection method of the present invention. Each binding agent or group of binding agents comprises polynucleotide(s) that is specific for a particular chromosome (and complementary to the sample and standard polynucleotide sequence from that chromosome), immobilised to a microparticle that is distinct from all other binding agents on the basis of size, fluorescent label, fluorescence intensity or a combination of these characteristics. These distinct microparticles may then be assessed individually for binding of the sample and standard. Accordingly, this provides simultaneous measurements for the relative frequency of multiple chromosomes in a sample.

In one aspect, the number of polynucleotides bound to a microparticle derived from a specific chromosome may be from about 1 to about 40,000. In a preferred aspect, the number of polynucleotides bound to the microparticle is from about 1 to about 3,000. In a most preferred aspect, the number of polynucleotides bound to a microparticle is about 2,000.

The method of the present invention has application to the detection of aneuploidy in any organism.

In preferred embodiment of the present invention, the subject is a human or other animal embryo generated using in-vitro fertilization.

The method of the present invention is able to detect aneuploidy in DNA extracted and/or amplified from a single cell. Therefore, the method of the present application is suitable, inter alia, for the detection of aneuploidy in animal embryos generated using in-vitro fertilization, prior to implantation of said embryo.

In addition to the detection of chromosome number in an organism, the present invention has application for the detection of non-dysjunction events in reproductive cells.

The present invention further provides a kit useful for simultaneously detecting aneuploidy for multiple chromosomes in organism, embryo or reproductive tissue.

A list of abbreviations used herein is provided in Table 1.

TABLE 1

Abbreviations

| ABBREVIATION | Description |
|---|---|
| IVF | In-vitro Fertilization |
| PCR | Polymerase Chain Reaction |
| 2n | the normal, euploid, number of chromosomes in a diploid organism |
| hCG | human chorionic gonadotropin |
| PLGA | poly d,l-lactic-co-glycolic acid |
| PMMA | pylymethylmethacrylate |
| TET | tetrachlorofluorescein |
| TAMRA | carboxytetramethylrhodamine |
| HEX | hexachlorofluorescein |
| JOE | 6-carboxy-4',5'-dichloro-2',7'-dimethoxyflourescein |
| FISH | Fluorescent in-situ Hybridisation |

DETAILED DESCRIPTION OF THE INVENTION

The present invention provides a method for the detection and sorting of microparticles in a mixture of microparticles. The method of the present invention allows for the detection and sorting of many distinct microparticle classes. Detection and sorting is on the basis of microparticle size, the fluorescence spectrum of any attached reporter molecule, the fluorescence intensity of the reporter molecule and discrimination of events passed on particle number. These microparticle classes have particular application as binding agents for the detection of aneuploidy in an organism or embryo of the organism. In humans, the detection and sorting of at least 24 classes of microparticles would be sufficient for a single tube method for the simultaneous detection of aneuploidy in all chromosomes, wherein each distinct microparticle class comprises a polynucleotide sequence complementary to, and specific for, a polynucleotide sequence that is unique to a particular human chromosome. Furthermore, using currently available technology, the present method has application for the simultaneous detection of aneuploidy in all chromosomes for an organism that has 216 or fewer pairs of chromosomes. Kits for the simultaneous detection of aneuploidy in one or more human chromosomes are also provided.

Before describing the present invention in detail, it is to be understood that unless otherwise indicated, the subject invention is not limited to specific formulations of agents, manufacturing methods, methodologies, or the like, as such may vary. It is also to be understood that the terminology used herein is for the purpose of describing particular embodiments only and is not intended to be limiting.

As used in the subject specification, the singular forms "a", "an" and "the" include plural aspects unless the context clearly dictates otherwise. Thus, for example, reference to "a microparticle" includes a single microparticle, as well as two or more microparticles.

In describing and claiming the present invention, the following terminology is used in accordance with the definitions set forth below.

"Subject" as used herein refers to an animal, preferably a mammal and more preferably a primate including a lower primate and even more preferably, a human who can benefit from the methods of the present invention. The subject may also be a non-animal such as a plant. A subject regardless of whether a human or non-human animal or embryo may be referred to as an individual, subject, animal, patient, host or recipient. The compounds and methods of the present invention have applications in human medicine, veterinary medicine as well as in general, domestic or wild animal husbandry and the horticultural/agricultural industry. For convenience, an "animal" specifically includes livestock species such as cattle, horses, sheep, pigs, camelids, goats and donkeys. With respect to horses, these include horses used in the racing industry as well as those used recreationally or in the livestock industry A human is the most preferred target. However, the method of the present invention is suitable for the detection of aneuploidy in any other non-human animal, including laboratory test animals.

Examples of laboratory test animals include mice, rats, rabbits, guinea pigs and hamsters. Rabbits and rodent animals, such as rats and mice, provide a convenient test system or animal model as do primates and lower primates. Non-mammalian animals such as avian species, zebrafish, amphibians (including cane toads) and *Drosophila* species such as *Drosophila melanogaster* are also contemplated.

In addition, for the purposes of the present invention, the term "subject" includes all born and unborn states of the organism in question. For example, with regard to humans, "subject" as used in this specification includes all pre-natal forms of a human including the zygote, blastocyst, embryo and fetus in addition to a post natal human. This term should also be understood to encompass zygotes, blastocysts and embryos of an organism generated and/or grown in-vitro, such as embryos generated as part of an in-vitro fertilization technique. Accordingly, all pre-natal forms and in-vitro embryos for other organisms are encompassed by the methods of the present invention. A subject may also be a plant species.

The present invention is predicated, in part, by a method for the multiplex detection and sorting of several distinct classes of microparticle from a mixture of microparticles on the basis of microparticle size, any label present on the microparticle, the intensity of the label and discrimination based on microparticle number.

Multiplexing is to be understood for the purposes of the present invention as the detection of multiple signals or results from a single sample, reaction, tube and the like. For example, multiplex polymerase chain reaction provides a method for the production and detection of multiple amplicons from a single reaction. For the purposes of the present invention, multiplexing is to be understood with reference to the simultaneous detection of signals associated with different microparticles in a mixture. Preferably, the multiplexed data relates to the size of the microparticle, any label attached to the microparticle and the intensity of any attached label and the relative numbers of microparticles.

Microparticles are beads and other particles, typically in a size range of 0.05 μm diameter to 1000 μm diameter. The material of the particle is commonly a compound selected from: glass, silica, alginate, gelatine, agar, cellulose, chitosan, poly-lactic acid, poly d,l-lactic-co-glycolic acid (PLGA), polystyrene, polymethylmethacrylate (PMA), melamine and gold. However, the present invention is not limited to microparticles of these materials, as any material to which a polynucleotide may be adsorbed, covalently bound, or otherwise attached, is contemplated by the present invention.

In a preferred embodiment of the present invention, the microparticles are silica microparticles.

Flow Cytometry may be defined as a technology to measure properties of cells as they move, or flow, in liquid suspension. An analogy may be made with a more familiar item of laboratory equipment, the microscope, to further describe this technology. Most microscopes have the following components:

A Light Source

The typical microscope uses a light bulb to illuminate the object. In the flow cytometer, the light source is often a laser. Lasers are used because they provide a very concentrated and intense beam of monochromatic light. The monochromatic character of the light is especially important in making fluorescence measurements.

The Stage

In a microscope, the stage is movable to allow passage of the object to the viewing field of an objective lens. In the flow cytometer, the cells or particles exist in liquid suspension. The liquid flows in response to air pressure, past an objective lens, thus carrying the cells or particles through the viewing field.

The Lens

In both the microscope and the flow cytometer, the lens collects light from the object.

The Filters

Some microscopes have filters to select those characteristics of the light that are most important to the observer. This is particularly true of fluorescence microscopes. In fluorescence, dye molecules are excited by light of a characteristic wavelength (or "color"), which then produce emitted light of a longer wavelength. The filters remove the excitation light to allow the emission light to be seen or measured.

The Detectors

In a microscope, the light detector is the observer. The flow cytometer uses highly sensitive light detectors called photomultiplier tubes, or "PMT"s. The detectors must be able to measure the brief flashes of emitted light from cells or particles that are moving one at a time through the viewing field of the objective lens at rates of up to several thousand per second.

Most flow cytometers can measure two kinds of light Light Scatter and Fluorescence.

Figure 1:
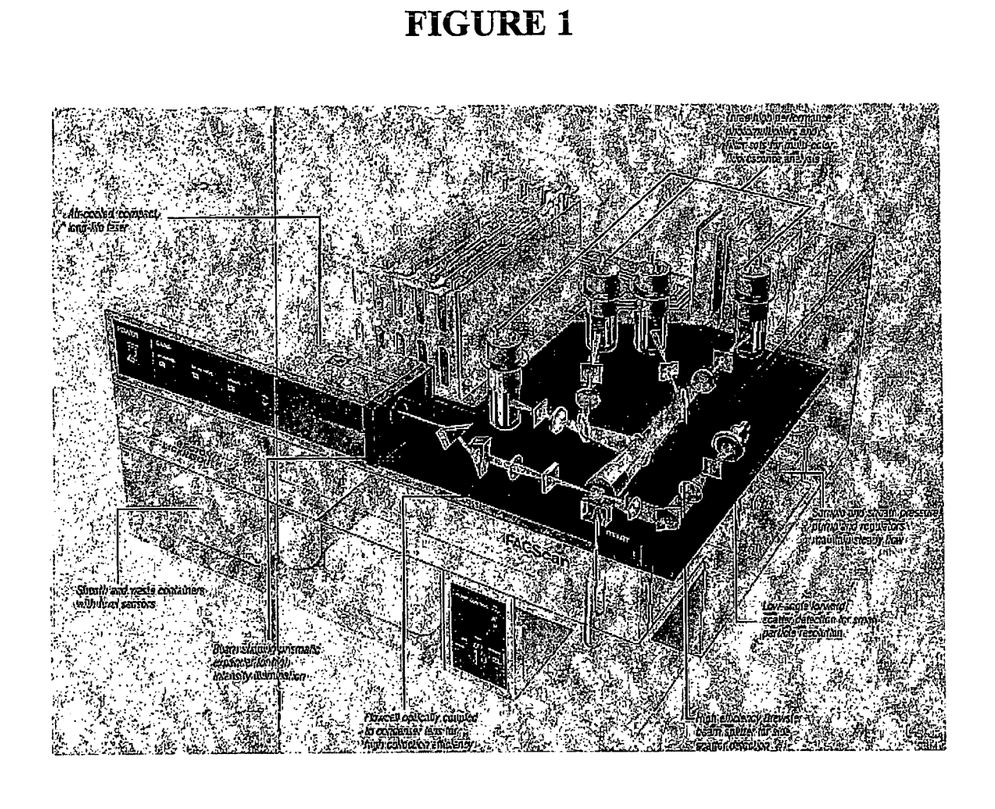
FIG. 1. Depicts a typical flow cytometer.

FIG. 1 shows the major components of one particular model of flow cytometer. One tank in the bottom supplies a buffer which carries the cells or particles through the instrument, while a second tank collects all of the waste fluid. The purpose of the carrier fluid (usually called sheath fluid) is to draw the suspension out so that the cells or particles pass in single file through the laser beam.

The laser at the left, front, illuminates the cells or particles flowing upward from the test tube with a blue beam. Forward light scatter is collected by a lens in-line with the laser beam (the laser beam itself is blocked by a small opaque bar) and reflected onto a light detector. Side light scatter and fluorescence is collected by a lens located at a right angle to the laser beam. This instrument can measure three colors of fluorescence in the green, orange, and red regions of the spectrum. The colors are separated by filters that either reflect or transmit only the desired wavelengths to the appropriate detectors.

Finally, all the electronic signals from the detectors are passed over to a computer (not shown) which records them and displays results. Since all measurements are made on each cell simultaneously, correlations between them can be determined. And, one measurement may be used to select a subset of cells for study using another measurement. For example, it would be possible to examine the green fluorescence for only large cells, identified by high forward light scatter.

In a preferred embodiment, microparticles are detected and/or sorted according to the method of the present invention using flow cytometry. The present invention, however, is in no way limited to the particular flow cytometry method or apparatus hereinbefore described. This example was provided only for illustrative purposes, and the present invention is not to be limited to an instrument or method according to the example provided.

Using flow cytometry, the size of a given particle or cell may be determined by the light scatter of the object.

Light scatter is the interaction of light and matter. All materials, including microparticles, will scatter light. It is composed largely of light that is reflected or refracted. The position from which an object is viewed often determines what can be told about it. In the flow cytometer, light scatter detectors are usually located opposite the laser (relative to the cell or particle), and to one side of the laser, in-line with the fluid-flow/laser beam intersection. The measurements made by these detectors are called forward light scatter and side light scatter, respectively.

Forward light scatter provides some information on the relative size of individual cells or particles, whereas side light scatter provides some information on the relative granularity of individual cells or particles. They are often used in combination to distinguish the different major categories of white cells in unseparated mammalian blood, but are useful in a wide variety of other assays as well, such as the determination of the size of a microparticle.

The present inventors have determined that flow cytometry is able to distinguish between microparticles of about 3.0 μm, about 3.5 μm, about 4.12 μm, about 5.0 μm, about 5.6 μm, about 6.2 μm and about 6.8 μm in diameter. Accordingly, the present inventors have identified that flow cytometry can differentiate up to at least 7 different sizes of microparticles.

In addition to size detection, flow cytometers typically have one or more lasers and detectors for the detection of fluorescence in a sample.

Fluorescence is the property of a molecule to absorb light of a particular wavelength and re-emit light of a longer wavelength. The wavelength change relates to an energy loss that takes place in the process. It is a characteristic that makes fluorescence extremely useful: filters may be used to exclude the excitation light from the light detector or the viewer. Thus, the only light measured or seen originates from the dye molecules. Interference from background or stray light striking the detectors is extremely low.

There are many fluorescent dyes that are useful for flow cytometry. They bind to a variety of cytochemical components, such as nucleic acids; proteins; specific cell-membrane, nuclear, and cytoplasmic receptors; intracellular ion molecules; and many more. A key property of a fluorescent dye which determines it's potential for use in a flow cytometric assay is the excitation wavelength: it must match the available wavelengths of the light source.

The present invention contemplates the labeling of a microparticle with a reporter molecule such as a fluorescent marker. Many different fluorescent markers will be familiar to those of skill in the art, and the choice of fluorescent marker in no way limits the invention. In a preferred embodiment of the present invention the fluorescent marker(s) used for the labelling of a microparticle comprise any fluorescent marker that can be attached to a microparticle and is excitable using a light source selected from the group below:

(i) Argon ion lasers—comprise a blue, 488 nm line, which is suitable for the excitation of many dyes and fluorochromes that fluoresce in the green to red region. Tunable argon lasers are also available that emit at a range of wavelengths (458 nm, 488 nm, 496 nm, 515 nm and others).

(ii) Diode lasers—have an emission wavelength of 635 nm. Other diode lasers which are now available operate at 532 nm. This wavelength excites propidium iodide (PI) optimally. Blue diode lasers emitting light around 476 nm are also available (iii) HeNe gas lasers—operate with the red 633 nm line.

(iv) HeCd lasers—operate at 325 nm.

(v) 100 W mercury arc lamp—the most efficient light source for excitation of UV dyes like Hoechst and DAPI.

In more preferred embodiments of the present invention the fluorescent markers are selected from: Alexa Fluor dyes; BoDipy dyes, including BoDipy 630/650 and BoDipy 650/665; Cy dyes, particularly Cy3, Cy5 and Cy 5.5; 6-FAM (Fluorescein); Fluorescein dT; Hexachlorofluorescein (HEX); 6-carboxy-4', 5'-dichloro-2', 7'-dimethoxyfluorescein (JOE); Oregon green dyes, including 488-X and 514; Rhodamine dyes, including Rhodamine Green, Rhodamine Red and ROX; Carboxytetramethylrhodamine (TAMRA); Tetrachlorofluorescein (TET); and Texas Red. In particularly preferred embodiments of the present invention, the markers are fluorescein and Cy5. Examples of fluorescent markers are described in Table 2.

TABLE 2

| Probe | Ex[1] (nm) | Em[2] (nm) |
|---|---|---|
| Reactive and conjugated probes | | |
| Hydroxycoumarin | 325 | 386 |
| Aminocoumarin | 350 | 455 |
| Methoxycoumarin | 360 | 410 |
| Cascade Blue | 375; 400 | 423 |
| Lucifer Yellow | 425 | 528 |
| NBD | 466 | 539 |
| R-Phycoerythrin (PE) | 480; 565 | 578 |
| PE-Cy5 conjugates | 480; 565; 650 | 670 |
| PE-Cy7 conjugates | 480; 565; 743 | 767 |
| APC-Cy7 conjugates | 650; 755 | 767 |
| Red 613 | 480; 565 | 613 |
| Fluorescein | 495 | 519 |
| FluorX | 494 | 520 |
| BODIPY-FL | 503 | 512 |
| TRITC | 547 | 574 |
| X-Rhodamine | 570 | 576 |
| Lissamine Rhodamine B | 570 | 590 |
| PerCP | 490 | 675 |
| Texas Red | 589 | 615 |
| Allophycocyanin (APC) | 650 | 660 |
| TruRed | 490, 675 | 695 |
| Alexa Fluor 350 | 346 | 445 |
| Alexa Fluor 430 | 430 | 545 |
| Alexa Fluor 488 | 494 | 517 |
| Alexa Fluor 532 | 530 | 555 |
| Alexa Fluor 546 | 556 | 573 |
| Alexa Fluor 555 | 556 | 573 |
| Alexa Fluor 568 | 578 | 603 |
| Alexa Fluor 594 | 590 | 617 |
| Alexa Fluor 633 | 621 | 639 |
| Alexa Fluor 647 | 650 | 688 |
| Alexa Fluor 660 | 663 | 690 |
| Alexa Fluor 680 | 679 | 702 |
| Alexa Fluor 700 | 696 | 719 |
| Alexa Fluor 750 | 752 | 779 |
| Cy2 | 489 | 506 |
| Cy3 | (512); 550 | 570; (615) |
| Cy3,5 | 581 | 596; (640) |
| Cy5 | (625); 650 | 670 |
| Cy5,5 | 675 | 694 |
| Cy7 | 743 | 767 |
| Nucleic acid probes | | |
| Hoeschst 33342 | 343 | 483 |
| DAPI | 345 | 455 |

TABLE 2-continued

| Probe | Ex[1] (nm) | Em[2] (nm) |
|---|---|---|
| Hoechst 33258 | 345 | 478 |
| SYTOX Blue | 431 | 480 |
| Chromomycin A3 | 445 | 575 |
| Mithramycin | 445 | 575 |
| YOYO-1 | 491 | 509 |
| SYTOX Green | 504 | 523 |
| SYTOX Orange | 547 | 570 |
| Ethidium Bromide | 493 | 620 |
| 7-AAD | 546 | 647 |
| Acridine Orange | 503 | 530/640 |
| TOTO-1, TO-PRO-1 | 509 | 533 |
| Thiazole Orange | 510 | 530 |
| Propidium Iodide (PI) | 536 | 617 |
| TOTO-3, TO-PRO-3 | 642 | 661 |
| LDS 751 | 543; 590 | 712; 607 |
| Cell function probes | | |
| Indo-1 | 361/330 | 490/405 |
| Fluo-3 | 506 | 526 |
| DCFH | 505 | 535 |
| DHR | 505 | 534 |
| SNARF | 548/579 | 587/635 |
| Fluorescent Proteins | | |
| Y66F | 360 | 508 |
| Y66H | 360 | 442 |
| EBFP | 380 | 440 |
| Wild-type | 396, 475 | 50, 503 |
| GFPuv | 385 | 508 |
| ECFP | 434 | 477 |
| Y66W | 436 | 485 |
| S65A | 471 | 504 |
| S65C | 479 | 507 |
| S65L | 484 | 510 |
| S65T | 488 | 511 |
| EGFP | 489 | 508 |
| EYFP | 514 | 527 |
| DsRed | 558 | 583 |
| Other probes | | |
| Monochlorobimane | 380 | 461 |
| Calcein | 496 | 517 |

[1]Ex: Peak excitation wavelength (nm)
[2]Em: Peak emission wavelength (nm)

In a preferred embodiment, the fluorescent label is BODIPY-F1 or tetramethyl rhodamine.

Two dyeing techniques are commonly used to fluorescently label microspheres—internal dyeing and external dyeing (surface-labeling). The two techniques produce beads with unique properties, each beneficial for different applications. Internal dyeing produces extremely stable particles with typically narrow fluorescent CV's. These particles often display a greater resistance to photobleaching. As the fluorophore is inside the beads, surface groups are available for use in conjugating ligands (proteins, antibodies, nucleic acids, etc.) to the surface of the bead. For this reason, internally labeled beads are typically used in analyte-detection and immunoassay applications. Surface-labeling involves conjugation of the fluorophore to the particle surface. Because the fluorophores are on the surface of the bead, they are able to interact with their environment just as the fluorophores on a stained cell. The result is a bead standard that exhibits the same excitation and emission properties as stained cell samples, under a variety of different conditions, such as the presence of contaminants or changes in pH. The "environmentally responsive" nature of surfacelabeled microspheres makes them ideally suited for mimicking biological samples. Externally labeled microspheres are frequently used as controls and standards in a number of applications utilizing fluorescence detection.

The present invention contemplates the association of a microparticle with a fluorescent label via any means. However, in a preferred embodiment, labels are associated with the microparticle using a method that allows beads to be labeled with a compound to give varying fluorescence intensities. More preferably, the labels are attached to the surface of the microparticle (external dyeing).

The present inventors have identified that it is possible to differentiate the intensity of a given fluorescent label on a microparticle of a particular size. The fluorescence intensity of a microparticle may be altered by changing the absolute amount, or concentration, of the fluorescent marker associated with the microparticle. Additionally, the present inventors have produced microparticles with up to six different fluorescence intensities for a given label.

However, the present invention is in no way limited by the number of distinct fluorescent intensities into which a label attached to microparticle at various concentrations, can be divided. Factors such as laser and photomultiplier technology influence the sensitivity of detection of a fluorescent label, and as such, influence how many distinct label intensities may be clearly defined. Accordingly, the present invention should not be limited by the number of distinct fluorescence intensities that can be achieved by labelling a microparticle with a fluorescent label.

Accordingly, by concatenation of the microparticle size data and fluorescence intensity data, the present invention provides a method for the differentiation of 36 different microparticle classes using a single fluorescent label.

Typically, flow cytometers, have more than a single detection channel. Many flow cytometers have four detection channels. The utilisation of multiple dyes on the microparticle detected by multiple detectors further expands the range of microparticles that can be differentiated according to the method of the present invention. For example, for a given bead size using a single detection channel, with 6 distinct quantifiable fluorescence intensities, 6 different microparticle types could be distinguished (on the basis of fluorescence intensity alone). However, a second channel, detecting a second dye on the microparticle, at a further 6 fluorescence intensity levels would expand the detectable range of particle classes to 36 (6 intensity levels in channel 1, by six intensity levels in channel 2). This data, combined with 6 distinct bead sizes, gives 216 categories into which a given dual-labelled microparticle may be sorted.

Accordingly, the present invention contemplates a method for the detection and sorting of labelled or unlabelled microparticles from a mixture of microparticles on the basis of one or more of the following characteristics:

(i) microparticle size
(ii) microparticle label
(iii) microparticle label intensity In a preferred embodiment, the microparticles are within the size range of 1-10 µm, specifically about 1, 2, 3, 4, 5, 6, 7, 8, 9, 10 µm, labelled with 0, 1, 2, 3, 4 distinct fluorescent labels which can be detected at 0, 1, 2, 3, 4, 5, 6, 7, 8, 9, 10 different levels of intensity by a light source and photodetector.

In a related embodiment, the present invention allows for discrimination of microparticles based on using different numbers of beads for different experiments. When using the number of microparticles to distinguish between samples, the numbers of microparticles in each experiment must be related in such as way that every number is unique from all other possible combinations of numbers. The approximate formula for ensuring that the numbers are unique from each other is $$Y_j = \sum_{j=1}^{1} Y_i \times 2.15$$

where $Y_j$ is the jth number cluster. The number of particles in this cluster is compiled by adding all previous number clusters and multiplying by 2.15.

A particularly preferred application of the present invention is the multiplex detection of aneuploidy in one or more chromosomes of an organism or embryo of an organism simultaneously.

For the purposes of the present invention aneuploidy is to be understood as any deviation from a euploid state in an organism, wherein euploidy is defined as a normal 2 n set of chromosomes. For example, in a human a normal, euploid 2 n number of chromosomes is 46. All conditions that deviate from this state are considered aneuploid for the purposes of the present invention. Exemplary aneuploid conditions in humans include monosomy and trisomy wherein a given chromosome is represented by one or three copies, respectively, instead of two copies as in the euploid state. Furthermore, aneuploidy in humans may be manifest as polyploidy wherein one (triploidy) or two (tetraploidy) complete sets of chromosomes are present in addition to the euploid complement of two.

In addition, for the purposes of the present invention, the term 'aneuploidy' should also be understood to incorporate partial monosomy conditions wherein a part of a chromosome is deleted.

This aspect of the present invention is predicated in part on the premise that if sampling equal amounts of DNA from each chromosome in a DNA sample, the relative contribution of each chromosome to the total DNA sample would be equal to 1/n of the total DNA, wherein n equals the number of chromosome pairs carried by the healthy diploid form of the organism. For example, in a non-aneuploid human subject each chromosome would contribute 1/23 of the total DNA in a given DNA sample. However, in a monosomic sample, the relative amount of DNA from that chromosome would represent 1/46 of the total DNA, while a trisomic chromosome would represent 2/23 of the total DNA.

Therefore, if a given amount of DNA from a known control diploid DNA is competed against a like amount of DNA from a given biological sample for a limiting number of binding targets, the DNA's should bind to the targets in their relative frequencies.

The present invention relates to a method for the simultaneous detection of aneuploidy in multiple chromosomes of a subject. The abundance of a given chromosome is represented by a nucleic acid sequence, referred to herein as a "sample", "DNA sample" or "polynucleotide sample". Any nucleic acid sequence that is unique and representative of a given chromosome may be suitable for the methods of the present invention. It will be easily ascertained by those of skill in the art whether a given nucleic acid sequence is unique and representative for a given chromosome.

Chromosome specific polynucleotide samples suitable for the present invention may be generated by any convenient means. Exemplary methods that in no way limit the invention include: isolation of chromosome specific polynucleotides from enzymatically or physically digested genomic DNA; amplification of chromosome specific polynucleotide sequences using PCR from genomic DNA; and identification of chromosome specific sequences via cloning and screening from genomic DNA.

Genomic DNA, suitable for the generation or identification of these chromosome specific polynucleotide samples, may be isolated using methods commonly used by those of skill in the art. The tissue used for the isolation of the genomic DNA would be dependent on the particular application of the method. For example, to test for aneuploidy in a post-natal organism, somatic cells of the organism would be suitable for the isolation of genomic DNA used to generate a sample according to the present invention. Alternatively, to detect non-disjunction events in reproductive cells, the DNA from the gametes of a given organism would need to be used for the generation of the sample. Finally, to screen for aneuploidy in a prenatal embryo, a blastomere would be the most appropriate tissue from which to generate the sample.

For the purposes of the present invention a "standard" is to be understood as an equivalent nucleic acid to the sample, but wherein the standard is generated from the genomic DNA of a known, non-aneuploid source. Therefore, in the case of a diploid organism, it is known that each chromosome is represented twice in the standard.

The term "equivalent", with regard to the sample and standard, is to be understood as equal binding to a given nucleic acid sequence, under the conditions used for hybridisation. For example, under very high stringency conditions, the nucleic acid sample, standard and binding agent may all have to have 100% identical polynucleotide sequences for equal binding of the sample and standard to the binding agent. However, at lower stringency, the sample and standard may have somewhat different polynucleotide sequences to each other, yet have equal binding affinity for the polynucleotide of the binding agent. Therefore, it is possible for one skilled in the art to determine what constitutes equivalency with regard to the standard and sample when hybridization conditions are considered. However, it is preferred that the sample and standard comprise identical polynucleotide sequences, and the binding agent comprises a polynucleotide sequence complementary to said sample and standard.

Partial loss of a given chromosome, known as deletion or partial monoploidy, may be detected using the method of the present invention when the sample of the chromosome is chosen from within a potentially deleted region. Furthermore, partial deletions may be confirmed by application of the method of the present invention using a marker within a putatively deleted region in comparison to a marker on the same chromosome outside the putatively deleted region. In this situation, a partial deletion of the chromosome would be detected as monoploidy using one marker on the chromosome and diploidy using another marker on the same chromosome.

The present invention further contemplates the labelling of a nucleic acid that is representative of a chromosome with a reporter molecule such as a fluorescent marker. Many different fluorescent markers will be familiar to those of skill in the art, and the choice of fluorescent marker in no way limits the invention. In a preferred embodiment of the present invention the fluorescent markers of the present invention comprise any fluorescent marker that can be attached to a polynucleotide and is excitable using a light source selected from the group below:

(i) Argon ion lasers—comprise a blue, 488 nm line, which is suitable for the excitation of many dyes and fluorochromes that fluoresce in the green to red region. Tunable argon lasers are also available that emit at a range of wavelengths (458 nm, 488 nm, 496 nm, 515 nm and others).

(ii) Diode lasers—have an emission wavelength of 635 nm. Other diode lasers which are now available operate at 532 nm. This wavelength excites propidium iodide (PI) optimally. Blue diode lasers emitting light around 476 nm are also available
(iii) HeNe gas lasers—operate with the red 633 nm line.
(iv) HeCd lasers—operate at 325 nm.
(v) 100 W mercury arc lamp—the most efficient light source for excitation of UV dyes like Hoechst and DAPI.

In more preferred embodiments of the present invention the fluorescent markers are selected from: Alexa Fluor dyes; BoDipy dyes, including BoDipy 630/650 and BoDipy 650/665; Cy dyes, particularly Cy3, Cy5 and Cy 5.5; 6-FAM (Fluorescein); Fluorescein dT; Hexachlorofluorescein (Hex); 6-carboxy-4', 5'-dichloro-2', 7'-dimethoxyfluorescein (JOE); Oregon green dyes, including 488-X and 514; Rhodamine dyes, including Rhodamine Green, Rhodamine Red and ROX; Carboxytetramethylrhodamine (TAMRA); Tetrachlorofluorescein (TET); and Texas Red. In particularly preferred embodiments of the present invention, the markers are fluorescein and Cy5.

In order to differentiate the standard from the sample for the purposes of the present invention, it is preferred that the labels for the sample and the standard have distinct emission spectra. In addition, when part of a multiplex reaction, as hereinbefore described, the fluorescence spectra of the label of the sample and standard must be distinct from the fluorescence spectrum or spectra of the label(s) attached to the binding agent.

The choice of method for the attachment of the fluorescent marker to the polynucleotide, or incorporation of said marker into the polynucleotide during synthesis or amplification in no way limits the present invention. All methods for fluorescently labelling a polynucleotide are contemplated by the present invention. Exemplary methods include both pre- and post-synthesis methods for labelling of polynucleotides. Pre-synthesis methods include labelling of a PCR primer that is subsequently used for amplification of, and thereby incorporated into, a polynucleotide via PCR. In this method, the fluorescent marker is typically attached to the 5' end of a primer suitable for the amplification of the polynucleotide. Also, a linker is typically used between the fluorophore and the polynucleotide molecule. Appropriate linker sequences will be readily ascertained by those of skill in the art, and are likely to include linkers such as C6, C7 and C12 amino modifiers and linkers comprising thiol groups. As will be readily ascertained, a primer may comprise the linker and fluorophore, or the linker alone, to which the fluorophore may be attached at a later stage. Post synthetic labelling methods include nick-labelling systems wherein a labelled polynucleotide is synthesised by Klenow polymerase from random primers. Fluorescent labelled nucleotides, or nucleotides comprising a linker group, may be incorporated into the Klenow polymerase synthesised polynucleotide during synthesis. However, it should be understood that the present invention is in no way defined or limited by the choice of labelling method.

Accordingly, the present invention therefore provides a method for detecting aneuploidy in one or more chromosomes of a subject simultaneously, said method comprising:
(i) producing reporter molecule-labelled polynucleotide saihples that are representative of the abundance of each chromosome in the subject;
(ii) producing equivalent, non-aneuploid polynucleotide standards for each chromosome, labelled with a different reporter molecule;
(iii) mixing the samples and standards with a limiting amount of binding agent for each chromosome, wherein the binding agents comprise a polynucleotide that is complementary to the sample and standard for each chromosome wherein the binding agent polynucleotide is immobilized onto a microparticle, and the microparticles associated with the polynucleotide sequence for each chromosome are distinct on the basis of size and/or fluorescent label and/or fluorescent label intensity;
wherein the fluorescent label on the microparticle, if present, has a distinct emission spectrum when compared to the spectra of the labels on both the sample and standard; and wherein aneuploidy is detected as non-equal binding of said sample and said standard to said binding agent.

Simultaneous detection of aneuploidy in multiple or all chromosomes of the organism is possible using the multiplex method of detection hereinbefore described. Each binding agent or group of binding agents comprises a polynucleotide that is specific for a particular chromosome (and complementary to the sample and standard polynucleotide sequence from that chromosome), immobilised to a microparticle. The microparticles representing each chromosome are that is distinct from each other on the basis of size, the fluorescent label (if any), fluorescence intensity or a combination of these characteristics. These distinct microparticles may then be assessed individually for binding of the sample and standard. Accordingly, this provides simultaneous measurements for the relative frequency of multiple or all chromosomes in a sample.

In order to detect aneuploidy in an organism, the method present invention is based on the competitive binding, to a limiting amount of complementary binding agent, of equal amounts of DNA from a sample and a standard of the same organism.

Therefore, the method of the present invention has application to the detection of aneuploidy in any organism. Many organisms have multiple copies of their chromosomes, and the present invention has application to detect aneuploidy in any organism that normally carries single or multiple copies of a chromosome. Exemplary organisms include, but in no way limit the invention: haploid organisms such as the males of certain species of wasp, bee and ant; triploid organisms such as oysters; diploid organisms such as animals, particularly humans; tetraploid organisms, including several plant species such as cyclamen and the American Elm, and some species of frog and toad; and hexaploid organisms such as the plant *Triticum aestivum*.

In a preferred embodiment of the present invention, the organism is a diploid animal. In an even more preferred embodiment, the animal is a mammal, such as a human or livestock animal. In a most preferred embodiment of the present invention the organism is a human. However, the present invention extends to non-animal species such as plants.

In an even further preferred embodiment of the present invention, the human subject is a human embryo generated using in-vitro fertilization.

In-vitro fertilization comprises four basic steps: ovary stimulation, egg retrieval, insemination, and embryo transfer. An example of the IVF procedure in humans is detailed below:
(i) Ovulation Induction—To stimulate the ovaries to produce more eggs, human menopausal gonadotropins are administered, which are concentrated forms of the natural hormones that stimulate ovulation. Gonadotropins cause several follicles to mature at once, ranging from two to thirty in humans. When the eggs are determined to be mature, one dose of human chorionic gonadotropin (hCG) is administered. hCG prepares the eggs for ovulation and fertilization. Here, it acts as a timekeeper indicating that approximately 40 hours from the moment of intake, ovulation will naturally occur. Therefore, egg retrieval must take place approximately 36 hours after this dose of hCG.

(ii) Egg Retrieval—A needle is placed into the ovary and fluid and eggs are removed from the follicles by a suction drive. The eggs are then placed into a test tube. On average, over two thirds of the follicles produce eggs.

(iii) Insemination and Fertilization—The eggs are allowed to mature for several hours before sperm are added, usually 6 to 8 hours after the retrieval. Insemination is simply the addition of the sperm to the culture media; each egg is isolated in its own dish and a defined number of sperm are placed with each one. The dishes are then placed in an incubator set at physiological temperature. Several hours later fertilization occurs when the sperm actually enter the egg. When this happens, the sperm loses its tail and its head enlarges. This stage is known as the 2PN stage because the two pro-nuclei have not fused yet. The embryo begins dividing, first into two and then four cells. Usually 36 to 48 hours after retrieval, the embryos cleave into four cells.

(iv) Embryo Transfer and Implantation—Embryo transfer (implantation) occurs 72 hours after egg retrieval. The embryos are drawn into a catheter and the fluid, containing the embryos, is deposited into the uterine cavity. The number of embryos transferred varies. After the transfer, it is up to the embryo to find and attach itself to the uterine wall.

In addition to assisting infertile humans reproduce, in-vitro fertilization has application in agriculture. For example in cattle, in-vitro fertilization has contributed to improvements in the genetic stock of cattle. Examples include:

(i) Older Cows—In the past, advanced age caused many cows with genetic merit to be eliminated from the breeding pool. These valuable old females may be able to generate a low-risk harvest of immature oocytes, or eggs.

(ii) Problem Cows—Females of all breeds and ages may have reproductive difficulties due to environmental causes: ovulatory failure, oviductal transport failure, disease/degeneration of the uterus, and non-responsiveness to stimulatory hormones. Even with these conditions, many cows can be managed to produce ovarian follicles which contain recoverable oocytes.

(iii) Healthy Cycling Females—Donor females can be enrolled in an in-vitro fertilization program simultaneously with the classical multiple ovulation and embryo transfer. By combining oocyte retrieval and the in-vitro fertilization program between rest periods in the superovulatory process, donors reach maximum success.

Accordingly, the method of the present invention should also be understood to encompass screening for aneuploidy in both human and non-human embryos generated using in-vitro fertilization techniques.

Current methods in the art for the detection of aneuploidy in embryos are based on post-implantation screens. Jenderney et al. (*Mol. Hum. Reprod* 6(9): 855-860, 2000) describe the method of using QF-PCR, specific for short tandem repeats on specific chromosomes, on samples of amniotic fluid. It is also possible to assess potential aneuploidy in a fetus from fetal cells in the maternal blood stream, using techniques such as fluorescent in-situ hybridization (FISH) (Bianchi et al., *Prenat. Diag.* 22(7): 609-615, 2002). However, as can be seen from the material sampled in these studies, these techniques are only suitable for the detection of aneuploidy in an embryo or fetus post-implantation.

The method of the present invention is able to detect aneuploidy in DNA extracted and/or amplified from a single cell. Therefore, the method of the present application is suitable, inter alia, for the detection of aneuploidy in animal embryos generated using in-vitro fertilization, prior to implantation of said embryo.

Single cells may be isolated from embryos using standard blastomere biopsy techniques, as will be known to those of skill in the art. Briefly, the blastomere biopsy procedure comprises the following steps:

(i) A 7-cell embryo, on Day 3 after IVF, is ready to be biopsied. It is held in place on a micromanipulator with a holding pipette.

(ii) A zona drilling pipette is used to drill a hole through the shell of the embryo (the zona) using acid Tyrode's.

(iii) The embryo biopsy pipette is then introduced through this opening, and gentle suction is applied to dislodge a single cell (a blastomere) from the embryo.

(iv) The biopsied embryo is then returned to the incubator for further culture. The blastomere can now be screened for aneuploidy according to the method of the present invention.

(v) Based on the analysis of the blastomere, corresponding non-aneuploid embryos are then selected for implantation.

Accordingly, the present invention provides a method for the detection of aneuploidy in an animal embryo generated by in-vitro fertilization, prior to implantation of the embryo.

In a preferred embodiment of the present invention, the animal embryo is a human embryo.

In addition to the detection of chromosome number in an organism, the present invention has application for the detection of non-dysjunction events in reproductive cells. In this aspect of the present invention, gametes of a said organism, preferably a human, may be tested for missing and/or duplicated chromosomes. The method of this aspect of the present invention would be largely similar to the methods hereinbefore described. Briefly, a nucleic acid representative of a given chromosome in a gamete is labelled with a reporter molecule such as a fluorescent marker, while an equivalent representative polynucleotide from a known non-aneuploid gamete is labelled with a different fluorescent marker. As with the method described for detection of aneuploidy in a somatic or embryogenic cell, the sample and standard polynucleotides are competitively bound to a limiting number of binding agents. A missing chromosome in the sample would be manifest as an increased detection of the standard on the binding agent. Duplication of a chromosome in the sample would be detected as an increased binding of sample to the binding agent. In the case where no non-dysjunction events have occurred in the sample, binding of the standard and sample to the binding agent should be approximately equal.

Binding agents contemplated by the present invention comprise a polynucleotide sequence immobilised to a substrate. The polynucleotide sequence of the binding agent comprises a polynucleotide sequence that is complementary to the nucleic acid sequence of the sample and standard, as described supra.

By complementary, it is to be understood that an immobilized polynucleotide of the present invention should bind to a chromosome-number representative polynucleotide of the sample and standard under low stringency conditions. Preferably the immobilized polynucleotide should bind to the sample and standard under medium stringency conditions, and most preferable the immobilized polynucleotide should bind to the sample and standard under high stringency conditions.

Reference herein to low stringency includes and encompasses from at least about 0 to at least about 15% v/v formamide (including 1%, 2%, 3%, 4%, 5%, 6%, 7%, 8%, 9%, 10% 11%, 12%, 13% and 14% v/v formamide) and from at least about 1 M to at least about 2 M salt for hybridization, and at least about 1 M to at least about 2 M salt for washing conditions. Generally, low stringency is at from about 25-30° C. to about 52° C., such as 25, 26, 27, 28, 29, 30, 31, 32, 33, 34, 35, 36, 37, 38, 39, 40, 41, 42, 43, 44, 45, 46, 47, 48, 49, 50, 51 and 52° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide, including 16%, 17%, 18%, 19%, 20%, 21%, 22%, 23%, 24%, 24%, 26%, 27%, 28%, 29% and 30% v/v formamide, and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C) % (Marmur and Doty, *J. Mol. Biol.* 5: 109, 1962). However, the $T_m$ of a duplex DNA decreases by 1° C. with every increase of 1% in the number of mismatch base pairs (Bonner and Laskey, *Eur. J Biochem.* 46: 83, 1974). Formamide is optional in these hybridization conditions. Accordingly, particularly preferred levels of stringency are defined as follows: low stringency is 6×SSC buffer, 0.1% w/v SDS at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

Polynucleotides may be encapsulated in microparticles during their production or may be attached to their surface post-production. The choice method used to associate the polynucleotide with the substrate will depend on the material used, as would be readily ascertained by the skilled artisan. In addition, further treatments, including silanization (coating of the substrate with silanes), may be performed on the microparticles prior to attachment of the polynucleotide in order to increase the binding of said polynucleotide to the microparticle.

Generally, microparticles may be coated with any compound that will covalently attach, or otherwise adsorb, to the surface of the microparticle, and in addition the agent should also have a chemical moiety for the attachment of a polynucleotide, such as a thiol, amine or carboxyl group. Examples of compounds with these characteristics include amino-terminated silanes such as amino-propyltrimethoxysilane or amino-propyltriethoxysilane. In addition to silanes, compounds such as poly-L-lysine that non-covalently attach to the glass surface and electrostatically adsorb the phosphate groups of the polynucleotide are also within the scope of the present invention. Therefore, other compounds, including other silanes suitable for the attachment of a polynucleotide to a surface would be readily identified by the skilled artisan, and the present invention is not limited by the choice of compound.

Methods of immobilizing a polynucleotide to a substrate are well known to those of skill in the art. For the purposes of the present invention, the actual substrate used for the immobilization of the binding agent polynucleotide does not affect the application of the present invention. Therefore the binding agent of the present invention encompasses a polynucleotide immobilized onto any substrate. Non-limiting examples of the immobilisation of polynucleotides on a substrate include: dipsticks; polynucleotides immobilized to membranes, including nitrocellulose and nylon, as used for Southern blotting; immobilized polynucleotides on glass or ceramic surfaces such as slides, as used in microarrays and the like; immobilized polynucleotides on bead based substrates such as microspheres which are suitable for analysis using flow cytometry.

The polynucleotide can be attached to the substrate using any convenient means, typically this is done by physical adsorption or chemical linking. In addition, substrates may be further coated with an agent that promotes or increases the adsorption or binding of the polynucleotide to the surface of the substrate, such as amino-silanes. However, other agents that perform this function will be readily identified by persons of skill in the art. In a preferred embodiment of the present invention the binding agent comprises a polynucleotide complementary to the polynucleotide of the sample and standard, wherein said binding agent polynucleotide is immobilized to a substrate, and the binding agent is compatible with flow cytometry.

In a more preferred embodiment, the binding agent comprises a polynucleotide immobilized to a microparticle. In an even more preferred embodiment the microparticle is a silica microparticle. In a yet more preferred embodiment said silica microparticle is silanized for the covalent attachment of a nucleic acid.

The detection of fluorescent compounds via excitation with a light source and detection at a specific wavelength can be applied to a variety of instruments. Specific light sources and photodetectors have been applied to microscopes for the techniques of epifluorescence microscopy and confocal laser microscopy. Flow cytometry also uses a fluorescence based detection system for cell sorting. In addition, a number of specialized detection apparatus have been developed for the purposes of assessing fluorescence for particular applications such as microarray readers. The method of the present invention is not defined by the method, and/or apparatus used for the detection of the fluorescent labels. The apparatus for detection will depend on the substrate to which the binding agent is attached. For example, binding agents comprising microparticles would likely be compatible with a flow cytometry based detection system, whereas a binding agent comprising a nucleic acid immobilized to a slide would likely be analysed using epifluorescence or laser scanning confocal microscopy. Finally, a number of binding agents arranged in an array on a slide would most likely be analysed using a specialized array reading apparatus. As can be ascertained from the above, the choice of detection method for the binding agent and bound labelled nucleic acid does not define or limit the present invention in any way, and is merely a function of the method of immobilization used for the binding agent.

However, in a further preferred embodiment of the present invention, the binding of the labelled sample and/or standard to the binding agent and/or the detection of the relative amount of labelled sample to standard bound to said binding agent are determined using a flow cytometer.

The present invention further provides a kit useful for simultaneously detecting aneuploidy in multiple or all chromosomes in an organism, embryo or reproductive tissue. The kit is conveniently in a multi-compartment form wherein a first compartment comprises one or more reporter molecule labeled, e.g. fluorescently labelled, oligonucleotide primer sets suitable for the amplification of chromosome specific genomic DNA sequences. A second compartment comprises oligonucleotide primers with identical sequence to the first compartment, but with a different reporter molecule. In a third compartment, are one or more binding agents, or groups of binding agents, comprising polynucleotide sequences complementary to the predicted amplicon(s) of the oligonucleotide primers. Each of these different polynucleotides is immobilised to a substrate, such as a microparticle. For each different binding agent polynucleotide, the microparticle to which it is attached is distinct on the basis of size, any attached label (e.g. a fluorescent label) and/or the intensity of the fluorescent label. These distinctions are such that the different classes of microparticle may be detected and sorted by flow cytometry. In addition to these components, instructions for the use of said kit are also included. It is not a requirement that the kit be in a multi-compartment form as it is possible to combine the contents of two or more of the compartments.

In a preferred embodiment, the sample, standard and microparticle binding agents are labeled with fluorescent labels. In a more preferred embodiment the emission spectra of the labels attached to the sample, standard and microparticle binding agent do not overlap.

The present invention is further described by the following non-limiting examples:

EXAMPLE 1

12-Plex Detection of Microparticles

Figure 2:
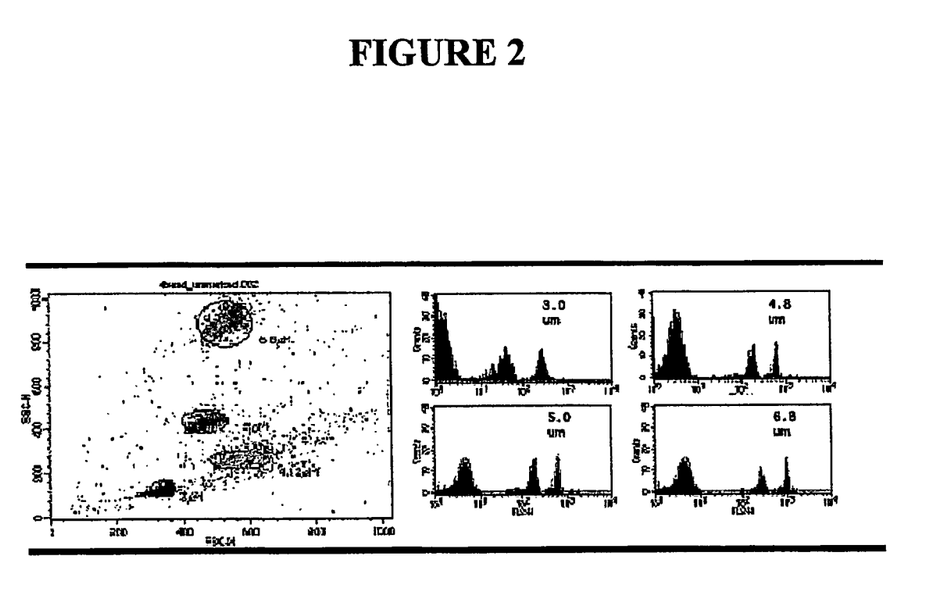
FIG. 2. Demonstrates a 12-plex discrimination of AmpaSand™ Beads using 4 bead sizes and 3 Fluorescence intensity levels in a single detection channel. Beads are separable by size (3.0, 4.12, 5.0 and 6.8 μm), as well as fluorescence intensity, in this case, no fluorescence, ⅓ fluorescence, and full fluorescence. Tetramethyl rhodamine is the marker used and is fluorescence level is measured in channel 2.
Figure 3:
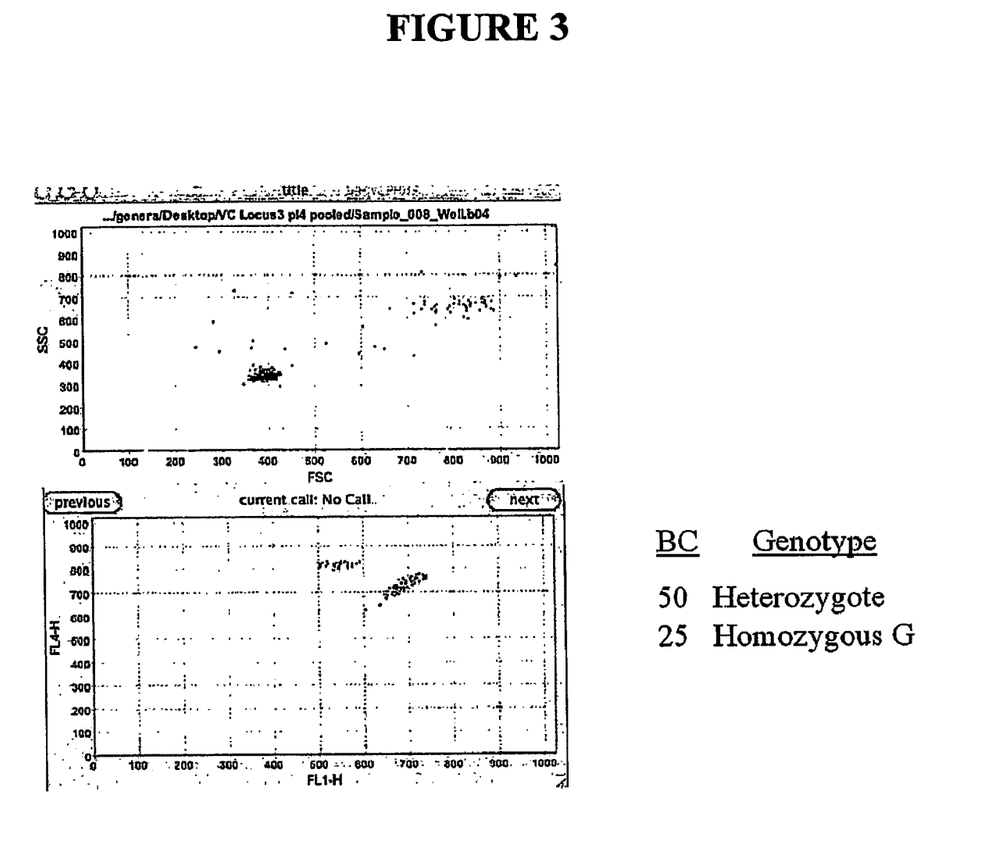
FIG. 3 is a representative example of a flow cytometric dot plot demonstrating the use of 2 different quantities of beads in the analysis of different samples. Beads are initially selected based on FSC and SSC and then analysed based on fluorescent markers. The lower plot is a dot plot where samples are compared, one of which is homozygous and one of which is heterozygous for the hGATA4 gene sequence. Analysis demonstrates 2 distinct groups, separated based on a nucleotide difference.
Figure 4:
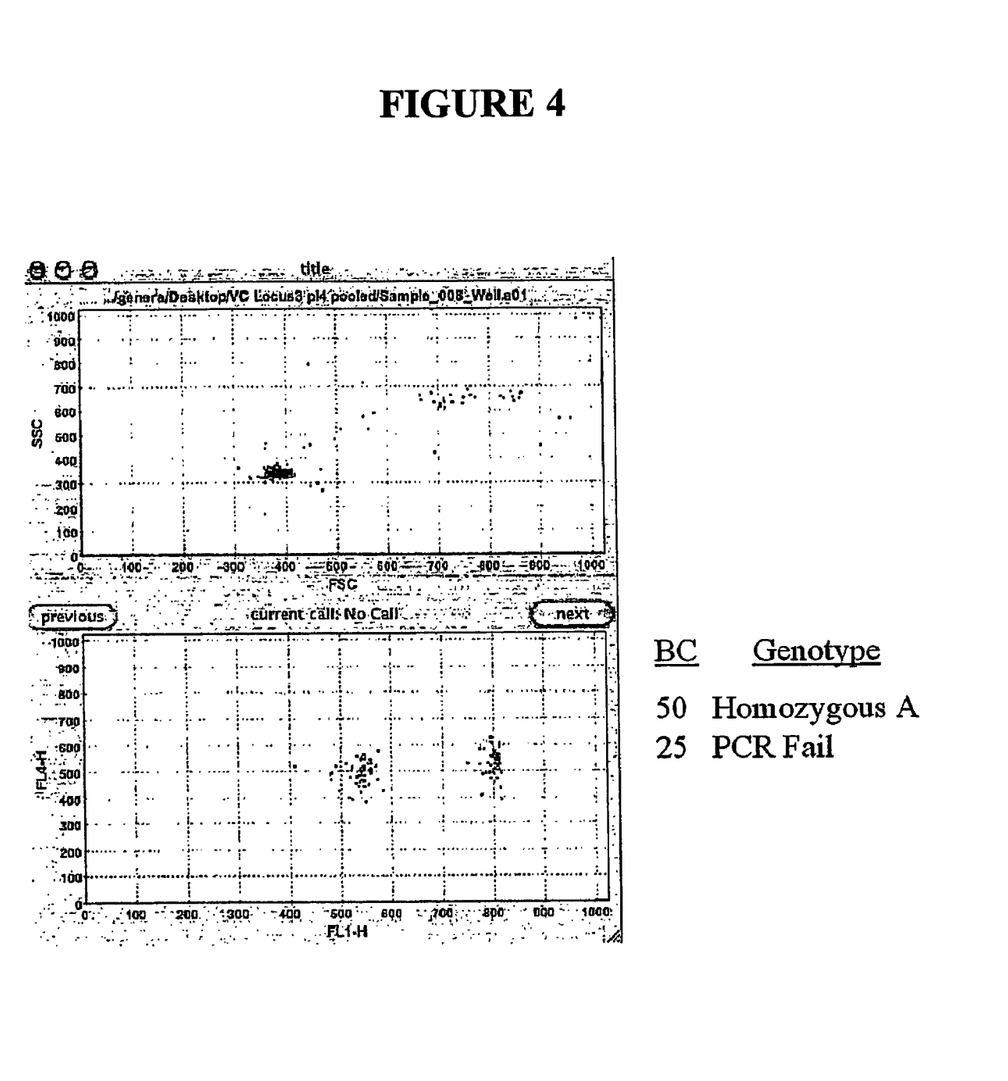
FIG. 4 is a representative example of a flow cytometric dot plot demonstrating the use of 2 different quantities of beads in the analysis of different samples. Beads are initially selected based on FSC and SSC and then analysed based on fluorescent markers. The lower plot is a dot plot where samples are compared, one of which is homozygous for "A" in the hGATA4 gene sequence and one of which is a negative control. Analysis demonstrates 2 distinct groups, separated based on a nucleotide difference.
Figure 5:
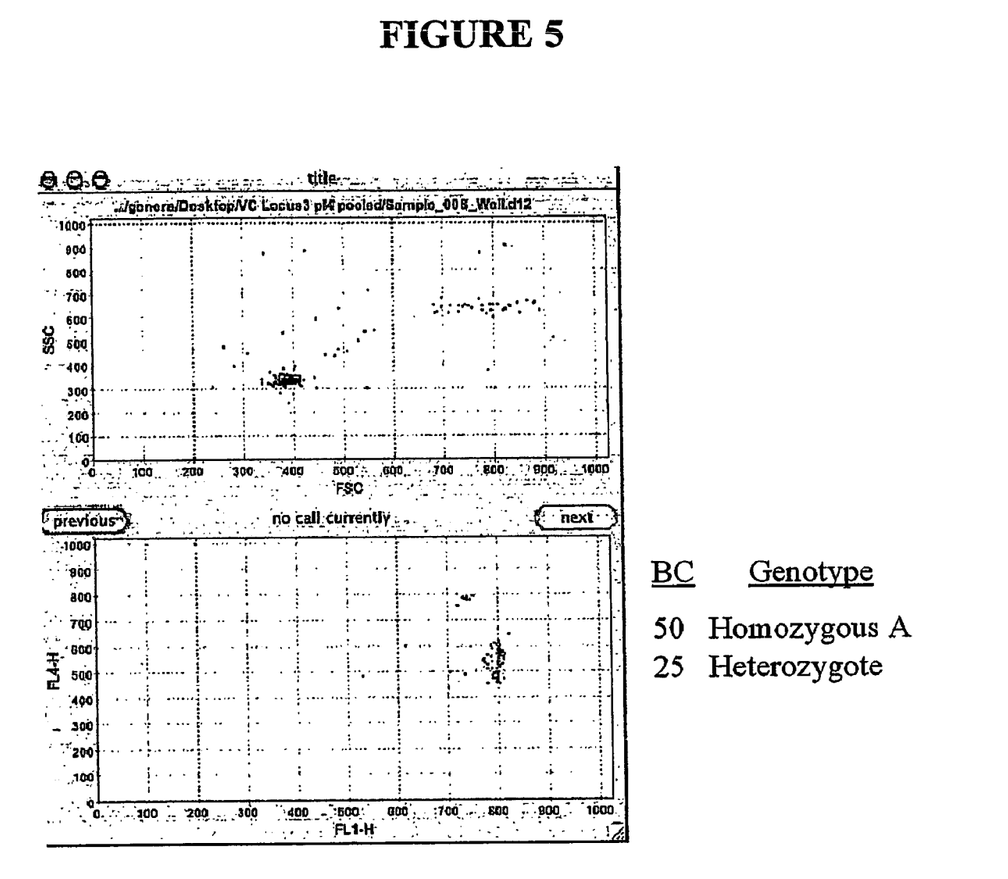
FIG. 5 is a representative example of a flow cytometric dot plot demonstrating the use of 2 different quantities of beads in the analysis of different samples. Beads are initially selected based on FSC and SSC and then analysed based on fluorescent markers. The lower plot is a dot plot where samples are compared, one of which is homozygous for "A" in the hGATA4 gene sequence and one of which is a heterozygous. Analysis demonstrates 2 distinct groups, separated based on a nucleotide difference.
Figure 6:
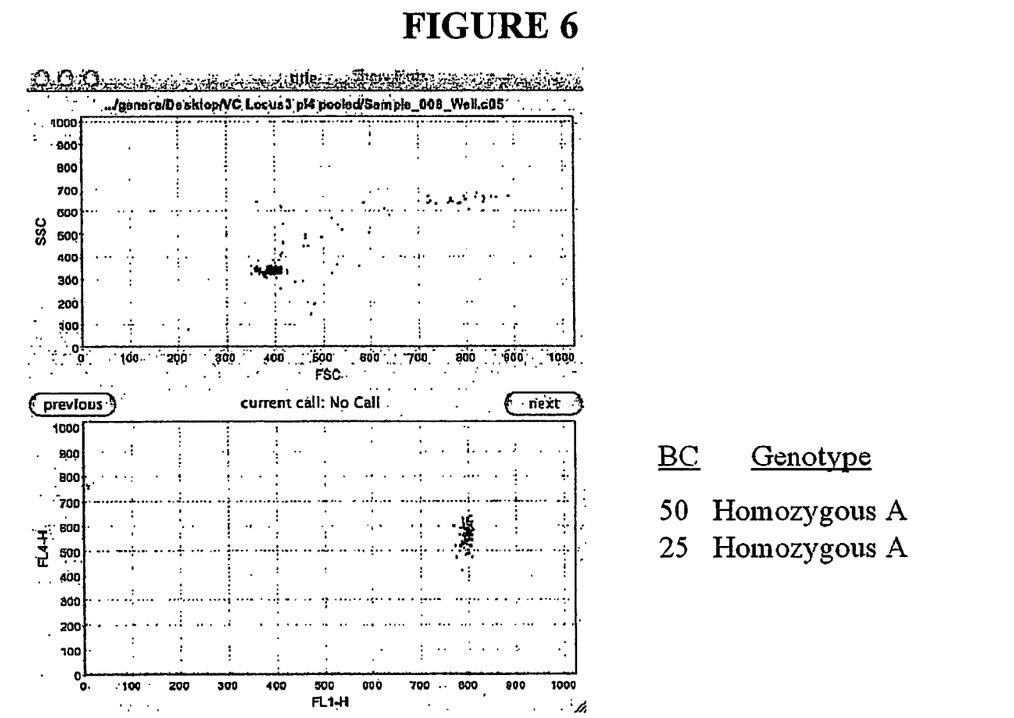
FIG. 6 is a representative example of a flow cytometric dot plot demonstrating the use of 2 different quantities of beads in the analysis of different samples. Beads are initially selected based on FSC and SSC and then analysed based on fluorescent markers. The lower plot is a dot plot where samples are compared, both of which are homozygous "A" in the hGATA4 gene sequence. Analysis demonstrates the presence of one group, which constitutes both samples.
Figure 7:
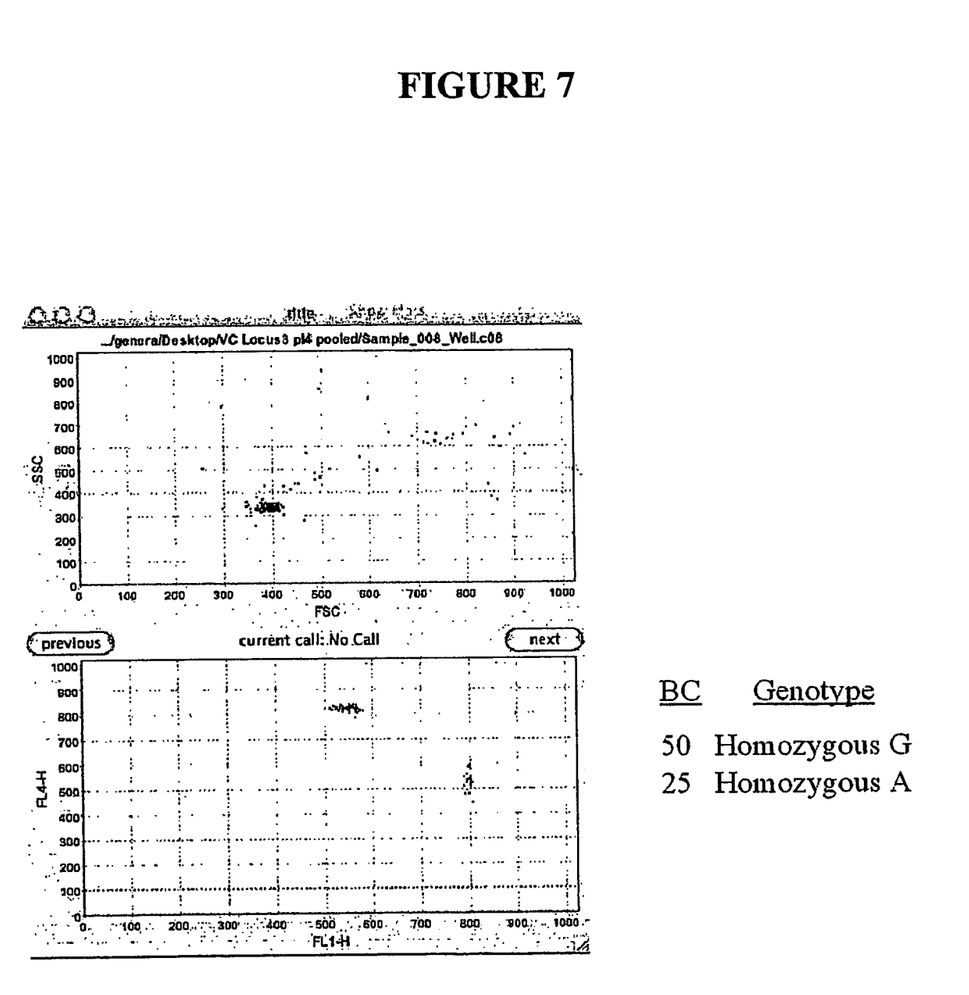
FIG. 7 is a representative example of a flow cytometric dot plot demonstrating the use of 2 different quantities of beads in the analysis of different samples. Beads are initially selected based on FSC and SSC and then analysed based on fluorescent markers. The lower plot is a dot plot where samples are compared, one of which is homozygous for "G" in the hGATA4 gene sequence and one of which is homozygous for "A". Analysis demonstrates 2 distinct groups, separated based on a nucleotide difference.

The ability of the method to differentiate between 12 different microparticle classes was tested. Microbeads of 3.0 μm, 4.12 μm, 5.0 μm and 6.8 μm were labeled with tetramethyl rhodamine at three different fluorescence intensity levels, 0, 33% and 100% to give 12 classes of microbead. These beads were then subjected to flow cytometry using a single detection channel. The results are depicted in FIG. 2.

EXAMPLE 2

Exemplary Microparticles for Simultaneous Detection of Aneuploidy in all Human Chromosomes Table 3 indicates an exemplary range of potential binding agents suitable for the simultaneous detection of aneuploidy in all human chromosomes. These microparticles comprise, 5 different size microbeads, labeled with a single fluorescent marker at 5 different intensity levels. This combination of bead size and marker intensity yields 25 possible bead classes which accommodates the 24 classes needed to examine all human chromosomes simultaneously.

EXAMPLE 3

Multiplex Analysis Using Number Clustering

Human hGATA4, exon 4 DNA was produced by PCR with a 5' phosphate on the forward primer. Allele specific probes were constructed for a Single Nucleotide Polymorphism within the PCR product. After PCR, excess primers and primer dimers were removed by ExoI digestion. Forward strand DNA was preferentially degraded by Lambda exonuclease. The ssDNA from the PCR was mixed with AmpaSand™ Beads (Genera Biosystems, Melbourne, Australia) customized with DNA identical to the phosphorylated forward primer in either a 25 bead per test or 50 bead per test configuration. Allele specific probes (SNP—A specific probe labelled with Tetramethylrhodamine (TMR) which emits in the yellow channel; and SNP-G specific probe labelled with Cy5 which emits in the red channel). After competitive hybridisation, experiments from 2 different experiments were combined and run simultaneously on a Becton-Dickinson FACSArray flow cytometer. Data was acquired and analyzed using the Showplots analysis package (Genera Biosystems). Briefly, the beads will cluster in 1 of four "pockets", depending on the state of the PCR product. If only "A" alleles (Homozygous A) are present in the PCR, only TMR will bind to the AmpaSand™ Beads and the beads will be yellow. If only "G" alleles are present (homozygous G) in the PCR, only Cy5 will bind to the beads and the beads will be red. If both alleles are present, the beads will be intermediate (a "half bright" red/a "half bright" yellow). If the sample is negative, there will be no fluorescence on the bead and the beads will cluster in a pocket which is very low in both channels.

Examples of the genotyping are shown in FIGS. 3-7. By using Number-Clustering multiplexing, the results can be easily assigned.

TABLE 3

Composition of an exemplary silica microparticle array suitable for the simultaneous detection of aneuploidy in humans.

| Polynucleotide complementary to: | Fluorescent label | Label intensity | Microparticle size |
|---|---|---|---|
| Chromosome 1 | BODIPY-F1 | 0% | 3.0 μm |
| Chromosome 2 | BODIPY-F1 | 25% | 3.0 μm |
| Chromosome 3 | BODIPY-F1 | 50% | 3.0 μm |
| Chromosome 4 | BODIPY-F1 | 75% | 3.0 μm |
| Chromosome 5 | BODIPY-F1 | 100% | 3.0 μm |
| Chromosome 6 | BODIPY-F1 | 0% | 4.12 μm |
| Chromosome 7 | BODIPY-F1 | 25% | 4.12 μm |
| Chromosome 8 | BODIPY-F1 | 50% | 4.12 μm |
| Chromosome 9 | BODIPY-F1 | 75% | 4.12 μm |
| Chromosome 10 | BODIPY-F1 | 100% | 4.12 μm |
| Chromosome 11 | BODIPY-F1 | 0% | 5.0 μm |
| Chromosome 12 | BODIPY-F1 | 25% | 5.0 μm |
| Chromosome 13 | BODIPY-F1 | 50% | 5.0 μm |
| Chromosome 14 | BODIPY-F1 | 75% | 5.0 μm |
| Chromosome 15 | BODIPY-F1 | 100% | 5.0 μm |
| Chromosome 16 | BODIPY-F1 | 0% | 5.9 μm |
| Chromosome 17 | BODLPY-F1 | 25% | 5.9 μm |
| Chromosome 18 | BODIPY-F1 | 50% | 5.9 μm |
| Chromosome 19 | BODIPY-F1 | 75% | 5.9 μm |
| Chromosome 20 | BODIPY-F1 | 100% | 5.9 μm |
| Chromosome 21 | BODIPY-F1 | 0% | 6.8 μm |
| Chromosome 22 | BODIPY-F1 | 25% | 6.8 μm |
| Chromosome X | BODIPY-F1 | 50% | 6.8 μm |
| Chromosome Y | BODIPY-F1 | 75% | 6.8 μm |

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of said steps or features.

BIBLIOGRAPHY

Bianchi et al., *Prenat. Diag.* 22(7):609-615, 2002

Bonner and Laskey, *Eur. J. Biochem.* 46:83, 1974

Jenderney et al., *Mol. Hum. Reprod.* 6(9) 855-860, 2000

Marmur and Doty, *J. Mol. Biol.* 5:109, 1962

The invention claimed is:

1. A competitive binding assay for detecting aneuploidy in a subject by simultaneously analyzing the relative frequency of all chromosomes in a sample from said subject, said method comprising:
   (i) producing a sample from a subject comprising fluorescently-labeled sample polynucleotides that are representative of the number of each chromosome in said subject;
   (ii) producing a standard comprising equivalent, non-aneuploid fluorescently-labeled standard polynucleotides for each chromosome, wherein the sample polynucleotides and the standard polynucleotides are labeled with fluorophores that have distinct emission spectra and the sample polynucleotides and standard polynucleotides are thereby distinguishable from one another;
   (iii) mixing said sample and standard under hybridization conditions with a limiting amount of binding agents for each chromosome, wherein the binding agents comprise nucleic acids that are complementary to the sample polynucleotides and standard polynucleotides for each chromosome and the nucleic acids are immobilized onto fluorescently-labeled microparticles,
   wherein each binding agent for each chromosome comprises a different fluorescently-labeled microparticle that has a distinct size and fluorescent label intensity,
   and wherein the fluorescent label on said microparticles has a distinct emission spectrum from that of the sample and standard; and
   (iv) detecting hybridization of the sample polynucleotides and the standard polynucleotides to the binding agents by detecting the fluorescent signals emitted by the sample polynucleotides bound to the binding agents and the standard polynucleotides bound to the binding agents and by detecting and distinguishing between the microparticles of the binding agents for each chromosome based on the size and fluorescent intensity of the microparticles,
   wherein the presence of aneuploidy in a subject is detected by detecting a difference in the fluorescent signal emitted by the sample polynucleotides bound to the binding agent as compared to that of the standard polynucleotides bound to the binding agent,
   and wherein the identity of the binding agent bound to the sample and standard polynucleotides is determined based on the size and fluorescent intensity of the microparticle, thereby simultaneously analyzing the relative frequency of all chromosomes in a sample from said subject.

2. The assay according to claim 1, wherein said subject is a diploid organism.

3. The assay of claim 2, wherein said diploid organism is selected from the group consisting of a mammal and a plant.

4. The assay of claim 3, wherein said mammal is selected from the group consisting of a human, a livestock animal and an embryo.

5. The assay of claim 4, wherein said livestock animal is selected from the group consisting of cattle, sheep and horses.

6. The assay of claim 4, wherein said embryo is generated using in vitro fertilization.

7. The assay of claim 6, wherein said aneuploidy is detected in said embryo prior to implantation of said embryo.

8. The assay according to claim 7, wherein said sample originates from a blastomere.

9. The assay according to claim 1, wherein said sample and said standard are produced from genomic DNA from a source selected from the group consisting of a somatic cell, a reproductive cell and a gamete.

10. The assay according to claim 1, wherein said microparticles are silica microparticles.

11. The assay of claim 10, wherein said silica microparticles are silanized.

* * * * *